(12) United States Patent
Cho et al.

(10) Patent No.: US 11,135,415 B2
(45) Date of Patent: Oct. 5, 2021

(54) MICRONEEDLE USING BIODEGRADABLE METAL

(71) Applicant: LABNPEOPLE CO., LTD., Gyeonggi-do (KR)

(72) Inventors: Sung Youn Cho, Gyeonggi-do (KR); Jong Tack Kim, Gyeonggi-do (KR); Hyun Wook Choo, Gyeonggi-do (KR)

(73) Assignee: LABNPEOPLE CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/091,718

(22) PCT Filed: Apr. 7, 2017

(86) PCT No.: PCT/KR2017/003792
§ 371 (c)(1),
(2) Date: Oct. 5, 2018

(87) PCT Pub. No.: WO2017/176077
PCT Pub. Date: Oct. 12, 2017

(65) Prior Publication Data
US 2019/0091456 A1    Mar. 28, 2019

(30) Foreign Application Priority Data

Apr. 7, 2016 (KR) .................. 10-2016-0042690
Nov. 30, 2016 (KR) .................. 10-2016-0162337
Apr. 6, 2017 (KR) .................. 10-2017-0044692

(51) Int. Cl.
*A61K 9/00* (2006.01)
*A61M 37/00* (2006.01)
(Continued)

(52) U.S. Cl.
CPC ....... *A61M 37/0015* (2013.01); *A61K 9/0021* (2013.01); *A61L 31/022* (2013.01);
(Continued)

(58) Field of Classification Search
CPC ................................ A61M 37/0015
See application file for complete search history.

(56) References Cited

U.S. PATENT DOCUMENTS

2006/0258973 A1* 11/2006 Volt .............. A61B 17/205
604/22
2011/0014181 A1* 1/2011 Thornton ............ A61K 45/06
424/130.1
(Continued)

FOREIGN PATENT DOCUMENTS

CN    104212998 A    12/2014
JP    2009-521250 A    6/2009
(Continued)

OTHER PUBLICATIONS

Persuad-Sharma et al, Biodegradable Magnesium Alloyws: A Review of Material Development and Applicaitons, J Biomim Biomater Tissue Eng, 2012, 12, 25-39 (Year: 2012).*
(Continued)

*Primary Examiner* — Paul W Dickinson
(74) *Attorney, Agent, or Firm* — Hauptman Ham, LLP (57) ABSTRACT

A microneedle using a biodegradable metal is represented by Chemical Formula 1 and is absorbed and degraded after subcutaneous or epithelial insertion to thus release metal ions and degradation products into the body. In Chemical Formula 1, a, b, and c represent wt % of respective ingredients, a+b+c=100 wt %, a or b has the highest value in the range of $0 \leq a \leq 100$, $0 \leq b \leq 100$, and $0 \leq c \leq 10$, and X is one or more selected from the group consisting of Ca, Fe, Mn, Si, Na, Zr, Ce, and P.

10 Claims, 11 Drawing Sheets

(51) Int. Cl.
*A61L 31/10* (2006.01)
*A61L 31/16* (2006.01)
*A61L 31/02* (2006.01)
*A61L 31/14* (2006.01)

(52) U.S. Cl.
CPC ............ *A61L 31/10* (2013.01); *A61L 31/148* (2013.01); *A61L 31/16* (2013.01); *A61M 2037/0023* (2013.01); *A61M 2037/0046* (2013.01); *A61M 2037/0061* (2013.01)

(56) References Cited

U.S. PATENT DOCUMENTS

2011/0172724 A1 7/2011 Hort et al.
2014/0093417 A1 4/2014 Liu et al.
2014/0097277 A1 4/2014 Kumta et al.

FOREIGN PATENT DOCUMENTS

| KR | 10-2008-0030553 A | 4/2008 |
|---|---|---|
| KR | 10-2011-0065391 A | 6/2011 |
| KR | 10-2015-0050586 A | 5/2015 |
| KR | 10-2015-0121053 A | 10/2015 |
| KR | 10-2016-0007923 A | 1/2016 |
| KR | 10-2016-0058261 A | 5/2016 |
| KR | 10-1622388 B1 | 5/2016 |

OTHER PUBLICATIONS

International Search Report in PC/KR2017/003792, dated Aug. 16, 2017, 6pp.
Ignacio et al., "The balneotherapy effect of hydrogen reduced water on UVB-mediated skin injury in hairless mice", Mol Cell Toxicol, 2013, The Korean Society of Toxicogenomics and Toxicoproteomics and Springer 2013, pp. 15-21, 7pp.
Yoon et al, "Histological Study on the Effect of Electrolyzed Reduced Water-Bathing on UVB Radiation-Induced Skin Injury in Hairless Mice", Pharmaceutical Society of Japan, vol. 34, No. 11, Nov. 2011, pp. 1671-1677, 7pp.

* cited by examiner

MICRONEEDLE USING BIODEGRADABLE METAL

RELATED APPLICATIONS

The present application is a National Phase of International Application Number PCT/KR2017/003792 filed Apr. 7, 2017, which claims priority to Korean Application Number 10-2016-0042690 filed Apr. 7, 2016, Korean Application Number 10-2016-0162337 filed Nov. 30, 2016, and Korean Application Number 10-2017-0044692 filed Apr. 6, 2017.

TECHNICAL FIELD

The present invention relates to an apparatus for delivering a drug to a body, and more particularly to a microneedle using a biodegradable metal and a microneedle patch including the same.

BACKGROUND ART

An oral administration method or an injection method of delivering a drug through a hole formed by piercing the skin using a needle has been used as a conventional drug delivery method. Among them, the injection method, which can be said to be an effective drug delivery method, may require an inoculator having knowledge of the use of a syringe, and may cause pain during injection, the inconvenience of repeated inoculation, and infection due to the reuse of needles attributable to poor management. Further, used syringes must be handled with special care as medical waste. In order to overcome these disadvantages, recently, a microneedle has been developed as a device that is capable of delivering a drug through the epidermis without stimulating the nociception nerves distributed in the skin. Many studies on the microneedle have been actively conducted, beginning with the proposal of the possibility of application of a microneedle array to drug delivery, the microneedle array including a silicon element and being manufactured using a semiconductor process technology by the Prausnitz Group of Georgia Institute of Technology in the USA in 1998. Since the microneedle must have sufficiently high physical strength to be inserted without being bent or broken when the microneedle is inserted into the skin, it is required to have properties suitable for controlling the strength and shape. Stainless steel has been used as the material of the microneedles in order to satisfy the above-described properties. However, there are problems in that inflammation occurs when small particles thereof remain in the body and in that penetration is not feasible in the case of polymers (PLA, PGA, biodegradable copolymers).

Korean Laid-Open Patent Application No. 2016-0058261 discloses a water-soluble microneedle, including polyglycolide (PGA), polylactide-glycolide copolymer (PLGA), hyaluronic acid, alginic acid, or pectin as a material therefor, and a method of manufacturing the same. Korean Patent No. 1622388 discloses a silicon microneedle stamp and a method of manufacturing the same. Korean Laid-Open Patent Application No. 2015-0121053 discloses a microneedle which is coated with a Japanese encephalitis vaccine antigen using silicon, silicon dioxide, ceramics, metals (stainless steel, titanium, nickel, molybdenum, chromium, and cobalt), and synthetic or natural resins as a material. However, as described above, they are problematic in that inflammation occurs or in that penetration into the skin is not feasible.

Therefore, the present inventors have made efforts to solve the above problems. As a result, the present inventors found that when a biodegradable metal such as magnesium, calcium, or zinc is used as the material of a microneedle, penetration into the skin is feasible. It was also found that when the biodegradable metal remains in a subcutaneous area, mineral ingredients thereof and hydrogen gas are provided to thus alleviate wrinkles and avoid inflammation reactions, which ameliorates the skin, thereby accomplishing the present invention.

DISCLOSURE

Technical Problem

Accordingly, the present invention has been made keeping in mind the disadvantages occurring in the conventional drug delivery devices, such as the occurrence of pain, concerns about infection, and medical waste, and an object of the present invention is to provide a microneedle including a metal material which has physical properties sufficient to penetrate the skin and which is used as a mineral for ameliorating the skin, and a microneedle patch including the same.

Technical Solution

In order to accomplish the above object, the present invention provides a microneedle using a biodegradable metal which is represented by Chemical Formula 1 and which is absorbed and degraded after subcutaneous or epithelial insertion to thus release magnesium or zinc metal ions and degradation products into the body.

[Chemical Formula 1]

In Chemical Formula 1, a, b, and c represent wt % of respective ingredients, a+b+c=100 wt %, a or b has the highest value in the range of $0 \le a \le 100$, $0 \le b \le 100$, and $0 \le c \le 10$, and X is one or more selected from the group consisting of Ca, Fe, Mn, Si, Na, Zr, Ce, and P.

In the present invention, in Chemical Formula 1, a, b, and c represent wt % of respective ingredients, a+b+c=100 wt %, (i) $90 \le a \le 100$, $0 \le b \le 10$, and $0 \le c \le 10$ or (ii) $0 \le a \le 10$, $90 \le b \le 100$, and $0 \le c \le 10$, and X is one or more selected from the group consisting of Ca, Fe, Mn, Si, Na, Zr, Ce, and P.

In the present invention, the biodegradable metal is pure Mg or pure Zn including inevitable impurities.

In the present invention, in the biodegradable metal, two or more metal phases generate a galvanic circuit to thus accelerate a degradation rate.

In the present invention, the microneedle includes an $Mg_2Ca$ phase.

In the present invention, the microneedle includes an MgZn phase.

In the present invention, the microneedle includes a $Ca_2Mg_6Zn_3$ phase.

In the present invention, in the microneedle, the surface of a metal is coated with another type of second metal in order to form a galvanic circuit.

In the present invention, the second metal is one or more metals selected from the group consisting of sodium, magnesium, potassium, iron, nickel, zinc, gallium, selenium, strontium, zirconium, molybdenum, niobium, tantalum, titanium, silicon, silver, gold, manganese, and calcium.

In the present invention, the microneedle is coated with a drug, or the drug is carried in the microneedle.

In the present invention, the microneedle is a thin-plate type.

The present invention also provides a microneedle patch including the microneedle.

Advantageous Effects

In a microneedle or a microneedle patch to which a biodegradable metal is applied according to the present invention, it is possible to realize strength sufficient to penetrate the skin due to the unique mechanical properties of the metal. In addition, after subcutaneous insertion to deliver a drug, minerals thereof and degradation products and gases generated during degradation are provided to the skin, whereby the skin is swollen to thus alleviate wrinkles.

BEST MODE

In the course of devising the present invention, an effort was made to confirm that when a microneedle is manufactured using one or more metals selected from the group consisting of Mg, Zn, Ca, Fe, Mn, Si, Na, Zr, Ce, and P as a material thereof, penetration into the skin is feasible, inflammation does not occur even though the metals remain in a subcutaneous area, and mineral ingredients thereof are provided to the skin to thus ameliorate the same.

In the present invention, a microneedle including magnesium or zinc as a single material and a microneedle including a biodegradable metal in which the above-described metal is mixed with another metal, such as calcium, as a material therefor, are manufactured. Further, the penetration ability and the skin-ameliorating ability of the microneedle that is manufactured are measured. As a result, it could be confirmed that the microneedle manufactured using magnesium, calcium, or zinc as the single material and the microneedle manufactured using an alloy in which the above-described metal is mixed with another metal in a predetermined range are excellent in terms of penetration ability and the skin-ameliorating ability.

Therefore, an aspect of the present invention relates to a microneedle using a biodegradable metal which is represented by Chemical Formula 1 and which is absorbed and degraded after subcutaneous or epithelial insertion to thus release magnesium or zinc metal ions and degradation products into a body.

$$Mg_a Zn_b X_c \qquad \text{[Chemical Formula 1]}$$

In Chemical Formula 1, a, b, and c represent wt % of respective ingredients, a+b+c=100 wt %, a or b has the highest value in the range of 0≤a≤100, 0≤b≤100, and 0≤c≤10, and X is one or more selected from the group consisting of Ca, Fe, Mn, Si, Na, Zr, Ce, and P.

It is preferable that the microneedle contain magnesium or zinc in the greatest amount. Therefore, in Chemical Formula 1, a, b, and c represent wt % of respective ingredients, a+b+c=100 wt %, (i) 90≤a≤100, 0≤b≤10, and 0≤c≤10 or (ii) 0≤a≤10, 90≤b≤100, and 0≤c≤10, and X is one or more selected from the group consisting of Ca, Fe, Mn, Si, Na, Zr, Ce, and P.

A typical microneedle is used for the purpose of delivering a drug to the skin. However, unlike the typical microneedle, the microneedle according to the present invention is absorbed and degraded after subcutaneous or epithelial insertion for drug injection, thus releasing metal ions and degradation products into the body.

Magnesium (Mg), calcium (Ca), and zinc (Zn), which are used as the material of the microneedle of the present invention, are biodegradable metals of the alkaline earth metal series, and react with water to thus release hydrogen gas as shown in the following equations. Therefore, when the microneedle using the above-described metals as the material is absorbed and degraded in a subcutaneous area, the microneedle may release ions and degradation products, hydrogen gas generated due to byproducts may cause a swelling effect in the subcutaneous area to thus induce a wrinkle alleviation effect, skin erythema caused by inflammation may be reduced, and skin damage caused by the sun may be prevented (YOON, K. S. et al., Histological study on the effect of electrolyzed reduced water-bathing on UVB radiation-induced skin injury in hairless mice. Biological and Pharmaceutical Bulletin 34, 1671-7, 2011; IGNACIO, R. M., et al., The balneotherapy effect of hydrogen reduced water on UVB-mediated skin injury in hairless mice. Molecular & Cellular Toxicology 9, 15-21, 2013).

ZnO and MgCl, which are byproducts generated due to insertion of magnesium (Mg) and zinc (Zn) into a living body, are capable of acting as a drug delivery enhancer that improves drug absorption even if they do not subcutaneously infiltrate the skin but merely remain on the surface thereof. Therefore, the needle including the biodegradable metal may further improve the effect of delivering the drug carried therein.

$Mg + 2H_2O \rightarrow Mg(OH)_2 + H_2(gas)$ $Ca + 2H_2O \rightarrow Ca(OH)_2 + H_2(gas)$ $Zn + 2H_2O \rightarrow Zn(OH)_2 + H_2(gas)$ In the present invention, the microneedle may be manufactured using magnesium (Mg) or zinc (Zn) as a single material, or may be manufactured using two or more metals as the material in order to accelerate a degradation rate in subcutaneous or epithelial areas, that is, in order to generate a galvanic circuit.

Figure 1:
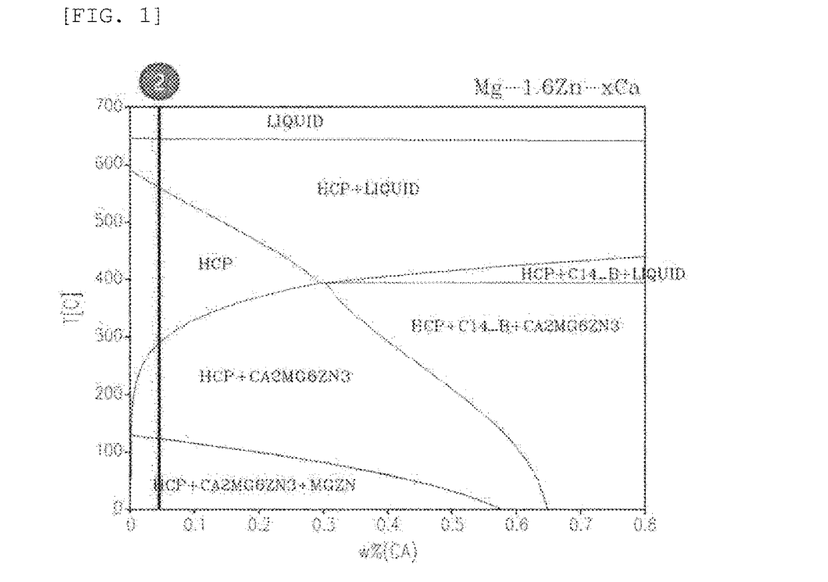
FIGS. 1 to 3 are phase diagrams according to contents of magnesium, zinc, and calcium (circle numbers mean Examples)
Figure 2:
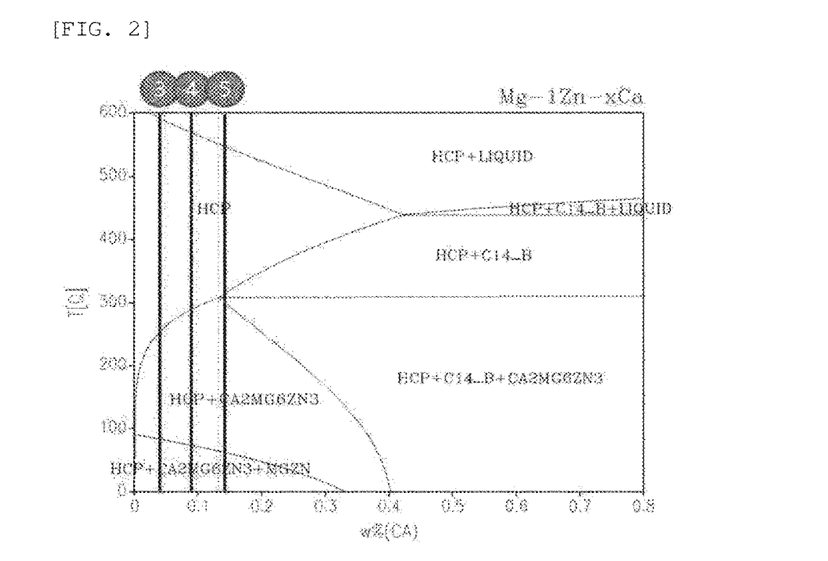
Figure 3:
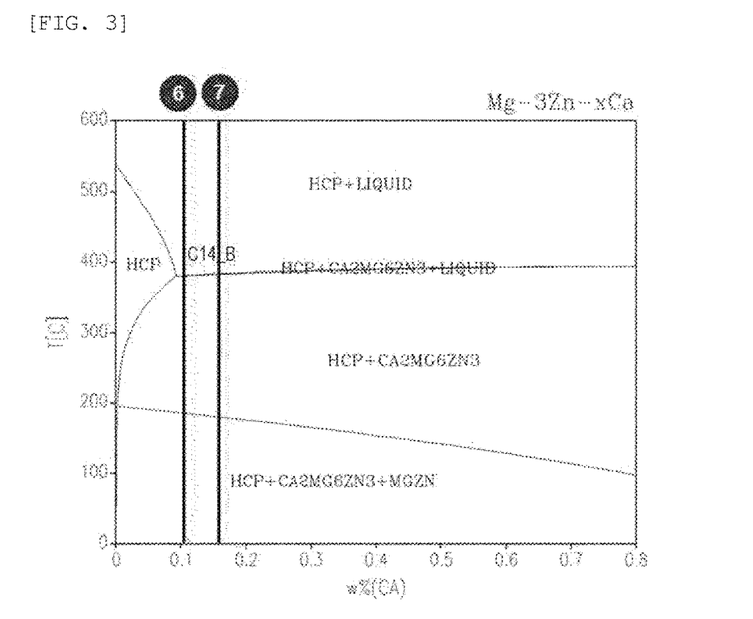

FIGS. 1 to 3 are phase diagrams according to contents of magnesium, zinc, and calcium. As shown in FIGS. 1 to 3, magnesium, zinc, and calcium may exist in various phases depending on the content thereof. $Mg_2Ca(C14\_B)$ may generate a galvanic circuit to thus increase a degradation rate.

In the present invention, the microneedle is characterized in that the surface of the biodegradable metal represented by Chemical Formula 1 is coated with another type of second metal in order to generate the galvanic circuit. Examples of the second metal may include sodium, magnesium, potassium, iron, nickel, zinc, gallium, selenium, strontium, zirconium, molybdenum, niobium, tantalum, titanium, silicon, silver, gold, manganese, and calcium, but are not limited thereto. Stainless steel should not be included when manufacturing the microneedle using iron (Fe).

Figure 4:
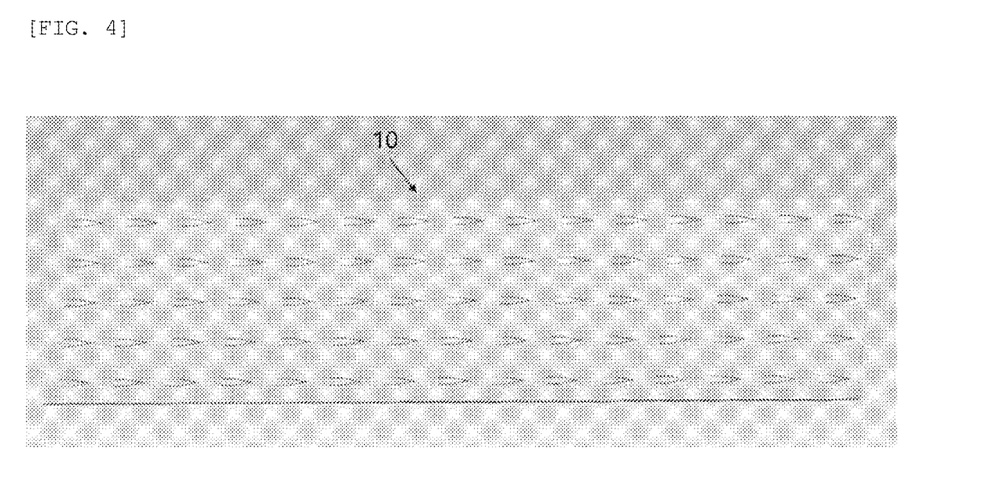
FIG. 4 is a developed view of a microneedle obtained by processing the microneedle for skin penetration and drug carrying on a sheet including a biodegradable metal.

In the present invention, the microneedle may be manufactured using a typical method for manufacturing a soluble microneedle in the industry such as laser cutting, a sheet-metal process, a casting processing method, and an etching processing method, and the manufacturing method thereof is not particularly limited. For example, as shown in FIG. 4, a thin-plate-type sheet 10 including a biodegradable metal may be manufactured, molded into a predetermined shape using a laser cutting machine (marking machine), and bent using a jig press, thereby manufacturing the microneedle.

Figure 5:
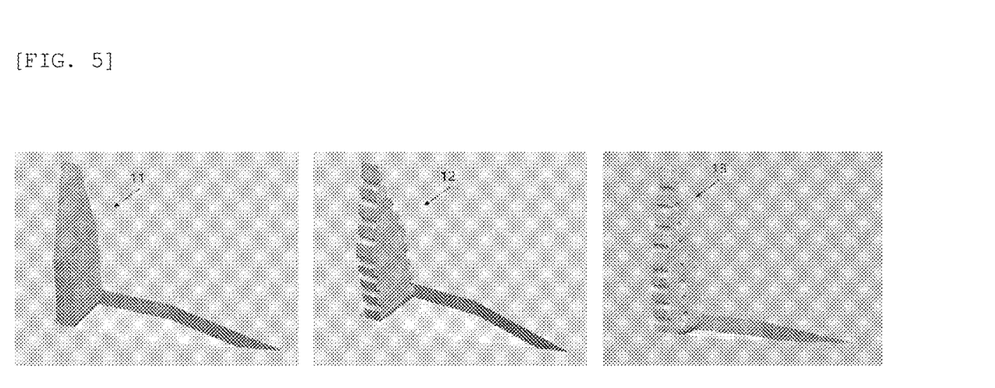
FIG. 5 shows schematic views of a microneedle which is subjected to bending processing for skin penetration, and a needle having a groove formed in an outer side thereof and a needle having grooves formed in outer and inner sides thereof for the purpose of improving a drug-carrying ability.

The microneedle is coated with a drug, or the drug is carried in the microneedle. FIG. 5 shows schematic views of a microneedle 11 which is subjected to bending processing for skin penetration, and a needle 12 having a groove formed in an outer side thereof and a needle 13 having grooves formed in outer and inner sides thereof for the purpose of improving a drug-carrying ability.

The drug may contain drug or genetic materials for disease prevention and therapy, and an EGF (epidermal growth factor) or hyaluronic acid for skin care may be carried therein. The microneedle, to which the biodegradable metal is applied and which is manufactured so that the drug is carried therein, may be coated using a dipping method (dip coating). A pocket for carrying the drug may be molded in the microneedle, whereby the drug is delivered into the body. When the pocket method is applied, the degradation rate of the biodegradable metal may be adjusted so that the portion of the drug carried in the microneedle patch is released immediately after attachment and the remaining portion of the drug is released when the pocket molded in the needle of the biodegradable metal is degraded, whereby the release rate of the drug may be controlled.

Figure 6:
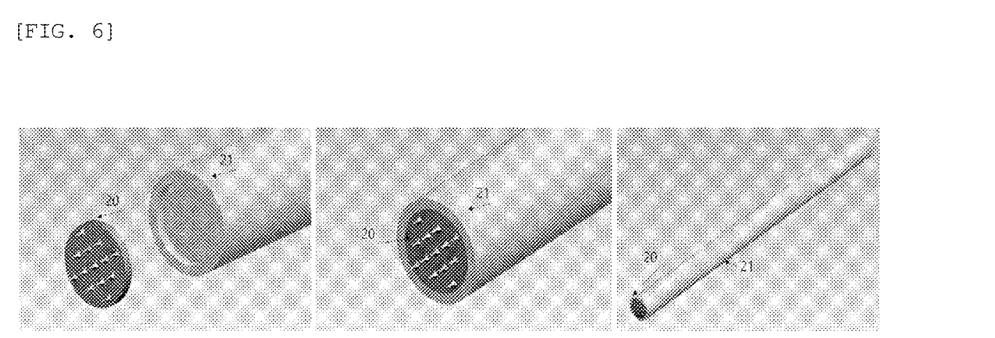
FIG. 6 shows schematic views of a tip-type microneedle and a microneedle holder.

The microneedle according to the present invention may be integrally constituted, or may be constituted by a microneedle 20 and a microneedle holder 21, as shown in FIG. 6. In the microneedle using the type of the microneedle holder 21, instead of simple injection of the drug after reaching the skin, the needle may be subcutaneously inserted and then twisted so that the needle artificially remains in a subcutaneous area.

Figure 7A:
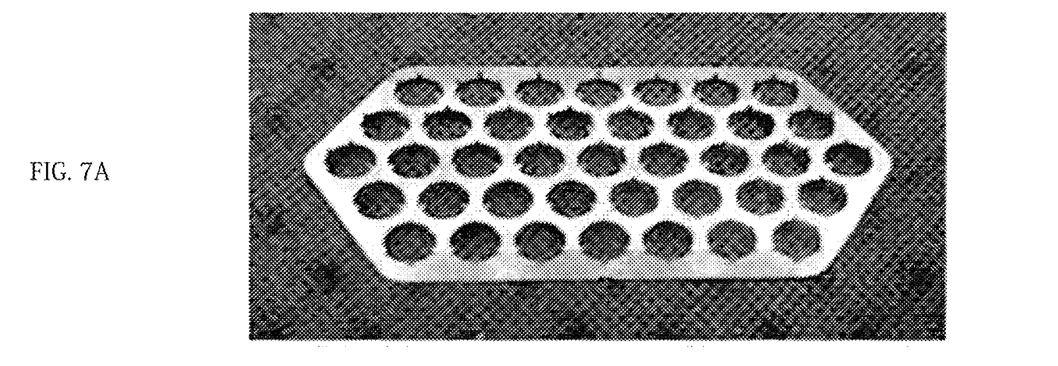
FIG. 7A shows a photograph of a prototype of a microneedle manufactured according to an embodiment of the present invention.
Figure 7B:
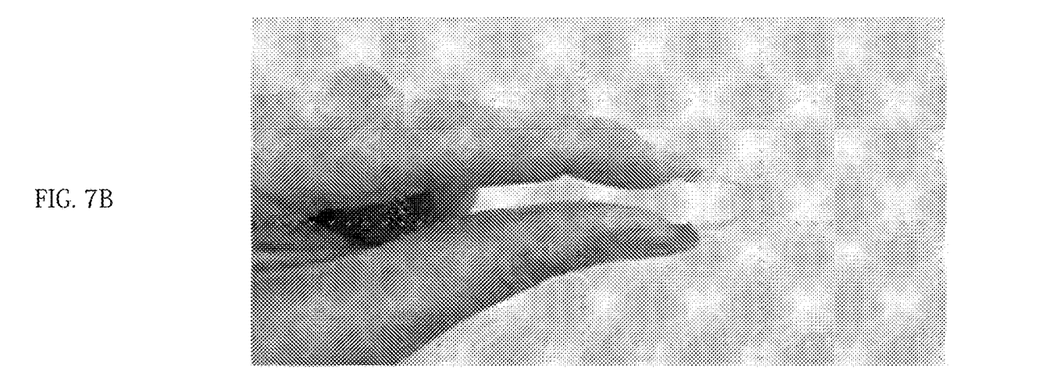
FIG. 7B is a photograph showing the elongation property thereof.

FIG. 7A shows a photograph of a prototype of a microneedle manufactured according to an embodiment of the present invention, and FIG. 7B shows a photograph showing the elongation property thereof.

The present invention also relates to a microneedle patch including the microneedle.

Figure 8A:
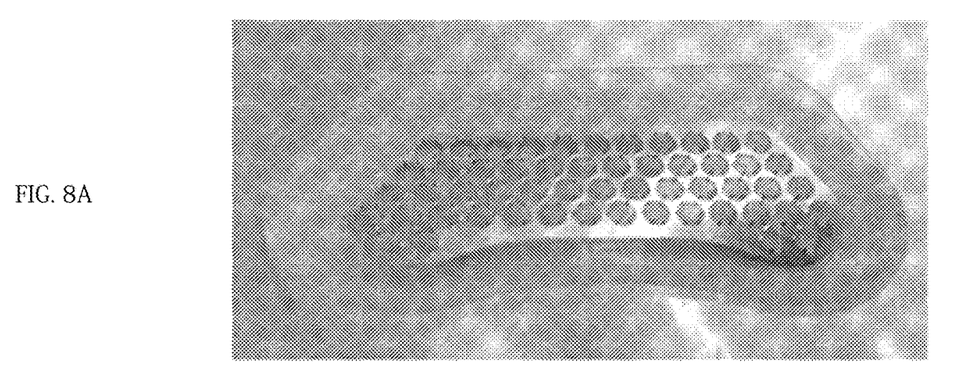
FIG. 8A and FIG. 8B are photographs of a microneedle patch manufactured according to the embodiment of the present invention (FIG. 8A: before use, FIG. 8B: after use)
Figure 8B:
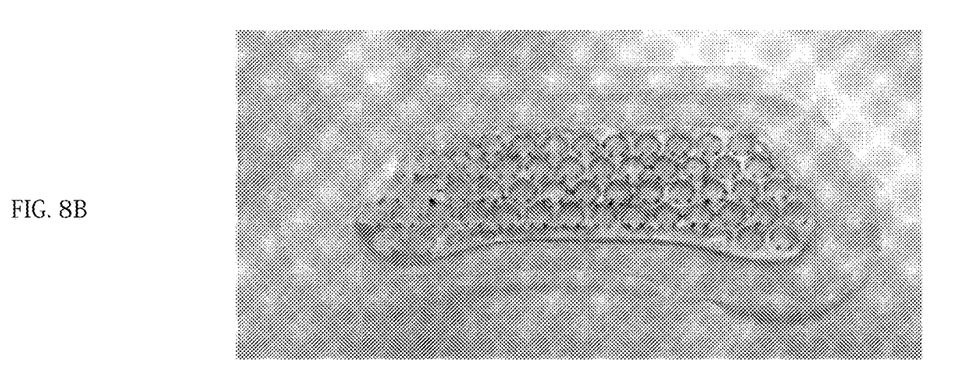

As shown in FIG. 8A and FIG. 8B, the microneedle patch is for fixing the microneedle to the skin, and is constituted by a microneedle and a patch unit that is formed on the opposite side of the microneedle. The patch unit may have any size, shape, and material without any particular limitation. As shown in FIG. 8B, the microneedle that is used may be ionized to thus be discolored in a subcutaneous area.

After the drug is injected into the microneedle sheet, the microneedle sheet may be attached to the skin and pressure may be applied thereto, thus subcutaneously injecting the drug through a slit formed in the microneedle.

MODE FOR INVENTION

Hereinafter, the present invention will be described in more detail with reference to Examples. It is to be understood by those skilled in the art that these Examples are for illustrative purposes of the present invention only and that the scope of the present invention is not construed as being limited by these Examples.

Figure 9A:
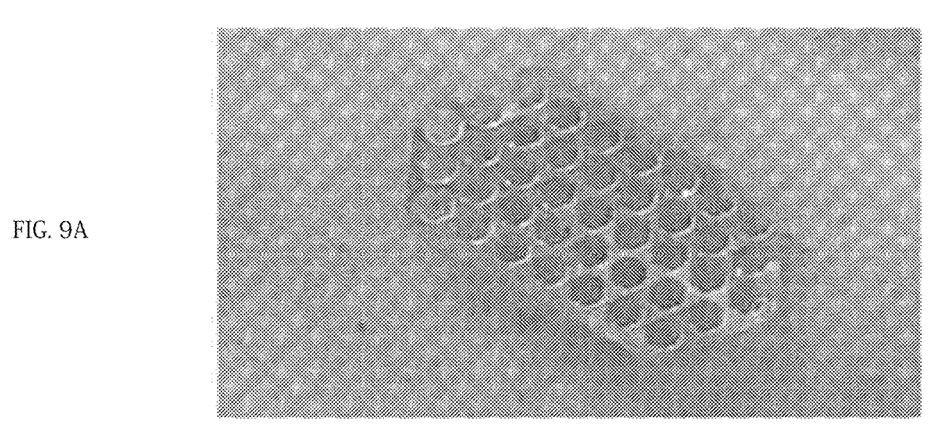
FIG. 9A and FIG. 9B are photographs showing the application of the microneedle manufactured according to the embodiment of the present invention to the skin.
Figure 9B:
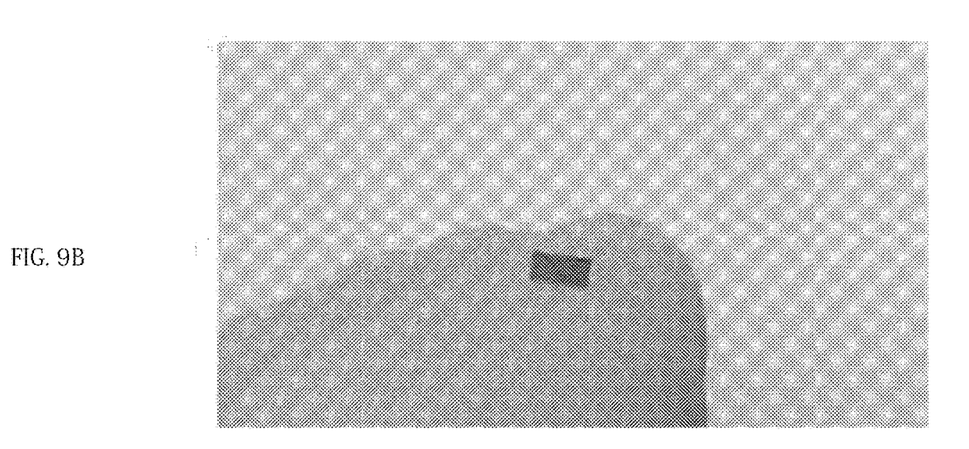

Examples 1 to 9: Microneedle Manufactured Using Magnesium or Zinc as Main Materials After a sheet was manufactured with the composition (wt %) shown in the following Table 1, a microneedle was manufactured using a laser marking machine (JTY FIBER MA20, JTY system) (FIG. 9A and FIG. 9B). The point angle of the microneedle was set to 15°, 30°, and 35°, and a needle height was set to 0.5 mm, 1.0 mm, and 1.5 mm.

TABLE 1

| Example | Mg | Ca | Zn |
|---------|------|------|--------|
| 1 | 99.99* | — | — |
| 2 | 98.35 | 0.05 | 1.60 |
| 3 | 98.95 | 0.05 | 1.00 |
| 4 | 98.9 | 0.10 | 1.00 |
| 5 | 98.85 | 0.15 | 1.00 |
| 6 | 96.9 | 0.10 | 3.00 |
| 7 | 96.85 | 0.15 | 3.00 |
| 8 | 0.00 | 0.00 | 99.99* |
| 9 | 10.00 | 0.00 | 90.00 |

*Pure metal containing inevitable impurities generated during manufacturing

Experimental Example 1: Evaluation of Skin Penetration Ability of Microneedle

Evaluation of skin penetration ability was performed on the microneedle of Example 1, having the poorest physical properties (tensile strength: average 212.09 MPa, elongation ratio: 11.32%, evaluation result of material owned by the inventor) among Examples 1 to 9, and the results are set forth in Table 2. The evaluation of the skin penetration ability was performed to determine whether the microneedle penetrated the skin surrounding the eyes of the human body and pig skin and whether penetration was maintained for 1 minute or more after the penetration into the coarse skin of the backs of human hands in the human body (see FIG. 9A and FIG. 9B).

TABLE 2

| Needle height (mm) | Point angle (°) | Interval between needles (mm) | Skin penetration ability |
|---|---|---|---|
| 0.5 | 15 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
|  | 30 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
|  | 35 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
| 1.0 | 15 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
|  | 30 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
|  | 35 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
| 1.5 | 15 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
|  | 30 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |
|  | 35 | 1.0 | Maintained after penetration into skin |
|  |  | 1.2 | Maintained after penetration into skin |
|  |  | 1.5 | Maintained after penetration into skin |
|  |  | 2.0 | Maintained after penetration into skin |

From Table 2, it could be confirmed that the microneedle of Example 1, having a point angle of 15 to 35° and a needle height of 0.5 to 1.5 mm, was excellent in skin penetration ability, and it was possible to deduce that the microneedles of Examples 2 to 9, in which calcium and zinc were added to increase tensile strength, will be excellent in skin penetration ability.

Experimental Example 2: Evaluation of Degradation Rate of Microneedle

Figure 10:
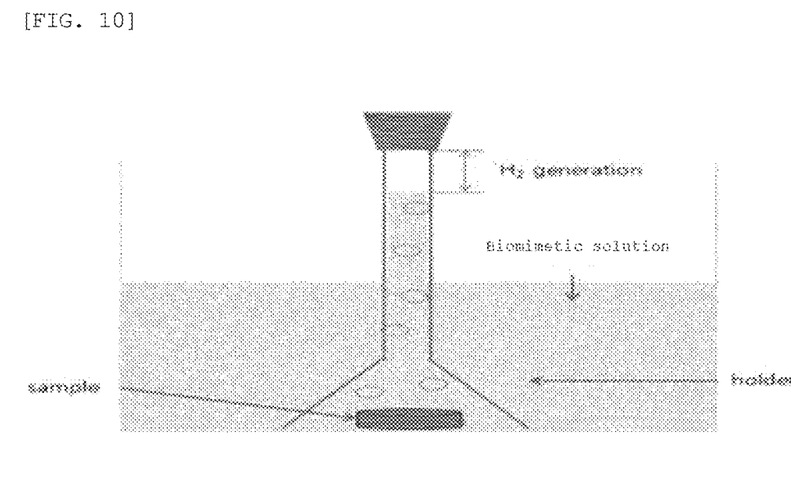
FIG. 10 is a schematic view of an apparatus (eudiometer) for measuring the amount of hydrogen generated depending on a dipping time of the microneedle manufactured according to the embodiment of the present invention.
Figure 11:
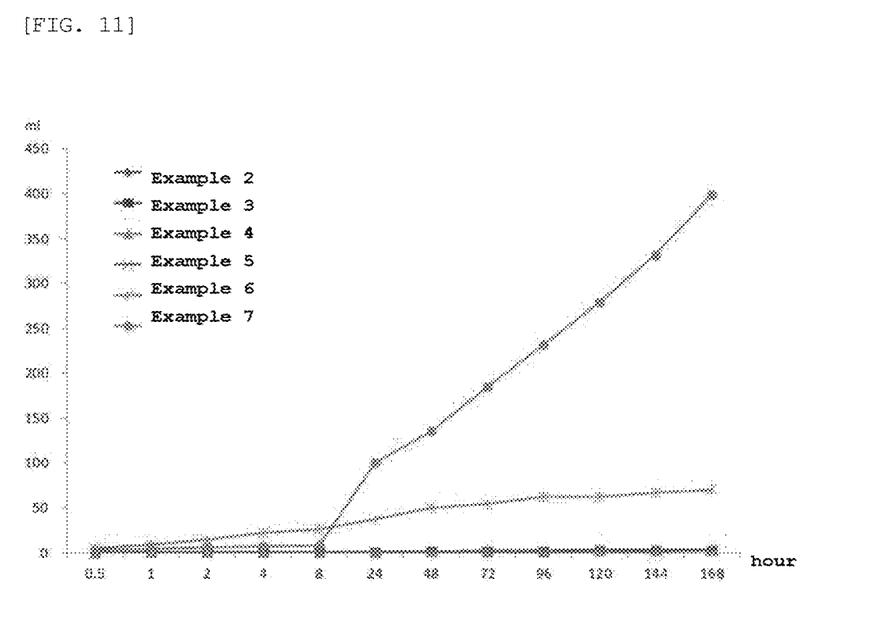
FIG. 11 is a graph showing the amount of hydrogen generated depending on the dipping time of the microneedle manufactured according to the embodiment of the present invention.

After the microneedles manufactured in Examples 2 to 7 were dipped in a eudiometer containing a biomimetic solution having the composition of Table 3 (see FIG. 10), the degradation rate was evaluated using the amount of hydrogen generated according to a dipping time, and the results are shown in FIG. 11.

TABLE 3

| Component | Mole concentration [mM/L] | Mass [g] |
|---|---|---|
| $CaCl_2 \cdot 2H_2O$ | 1.26 | 0.185 |
| KCl | 5.37 | 0.400 |
| $KH_2PO_4$ | 0.44 | 0.060 |
| $MgSO_4 \cdot H_2O$ | 0.81 | 0.200 |
| NaCl | 136.89 | 8.000 |
| $Na_2HPO_4 \cdot 2H_2O$ | 0.34 | 0.060 |
| $NaHCO_3$ | 4.17 | 0.350 |
| D-Glucose | 5.55 | 1.000 |

As shown in FIG. 11, the microneedles of Examples 2 to 5, in which an $Mg_2Ca$ phase was not generated, showed the amount of hydrogen gas generated according to stable degradation. However, it could be confirmed that, in the case of the microneedles of Examples 6 and 7, in which the $Mg_2Ca$ phase was generated, the degradation rate was increased.

Example 10: Manufacture of Microneedle Patch

A hydrocolloid patch coated with an adhesive was attached to the side that was opposite the needle side of the microneedle manufactured in Example 1, thus manufacturing a microneedle patch. The manufactured microneedle patch was packaged and sterilized.

Experimental Example 3: Evaluation of Skin Irritation by Microneedle Patch

A clinical skin research center was commissioned for evaluation in order to check the presence of primary irritation on the human skin by the microneedle patch manufactured in Example 10.

<Test Method>
(1) Application Region of Test Material
A flat region of a back except for the vertebra of a test subject, in which there was no coloration or skin damage.
(2) Before Application of Test Material
The test region was photographed, and questionnaire assessment was performed on the skin condition of the test subject.
(3) Application of Test Material
After the test material was loaded in an amount of 20 µl into an IQ chamber, the resultant chamber was adhered to the skin and then fixed using a 3M micropore tape.
The IQ chamber to which the test material was applied was applied to the test region for 24 hours.
After 24 hours, the IQ chamber was removed. After one hour, the region to which the test material was applied was photographed, and the degree of skin reaction was evaluated by a tester.
24 hours after the IQ chamber was removed, the region to which the test material was applied was photographed, and the degree of skin reaction was evaluated by the tester.
(4) Test Subject
The average age of thirty test subjects was full 39.47 years, and the test subjects were constituted by 6 persons in their 20s, 5 persons in their 30s, 18 persons in their 40s, and 1 person in his/her 50s. The sex composition thereof included 3 males and 27 females.

<Evaluation Method>

(1) Pre-Survey of Test Subjects: The Test Subjects were Surveyed Using a Questionnaire.

Skin type: Whether the skin was dry, moderately dry, neutral, moderately oily, oily, or problematic Skin condition: Skin disease, itching, prickling, erythema, cosmetic side effects, medical side effects, photosensitivity, and atopy experiences (2) Evaluation Items Evaluation using tester's naked eyes: The degree of skin irritation occurring at the application region of the test material (3) How to Evaluate the Degree of Skin Irritation In the evaluation using the tester's naked eyes, the degree of skin reaction was read based on Frosch & Kligman, CTFA guidelines, and a skin irritation index was calculated. The degree of skin irritation of the test material was classified with reference to a skin-irritation-index table (Table 4) generated by applying a Draize method.

TABLE 4

| Skin irritation index | Classification |
|---|---|
| 0.00 to 0.25 | Non-irritative |
| 0.26 to 1.00 | Mildly irritative |
| 1.01 to 2.50 | Moderately irritative |
| 2.51 to 4.00 | Strongly irritative |

The microneedle patch was applied for 24 hours. The skin reactions 1 hour and 24 hours after the patch was removed were evaluated using the tester's naked eyes, thus judging the skin irritation index and the degree of skin irritation. As a result, the irritation was judged to be mild (Table 5).

TABLE 5

| | Skin irritation index | | | |
|---|---|---|---|---|
| Test product | After 1 hour | After 24 hours | Degree of skin Total irritation | |
| Microneedle patch | 0.93 | 0.33 | 0.63 | Mildly irritative |

Experimental Example 4: Clinical Evaluation of Microneedle Patch

Figure 12:
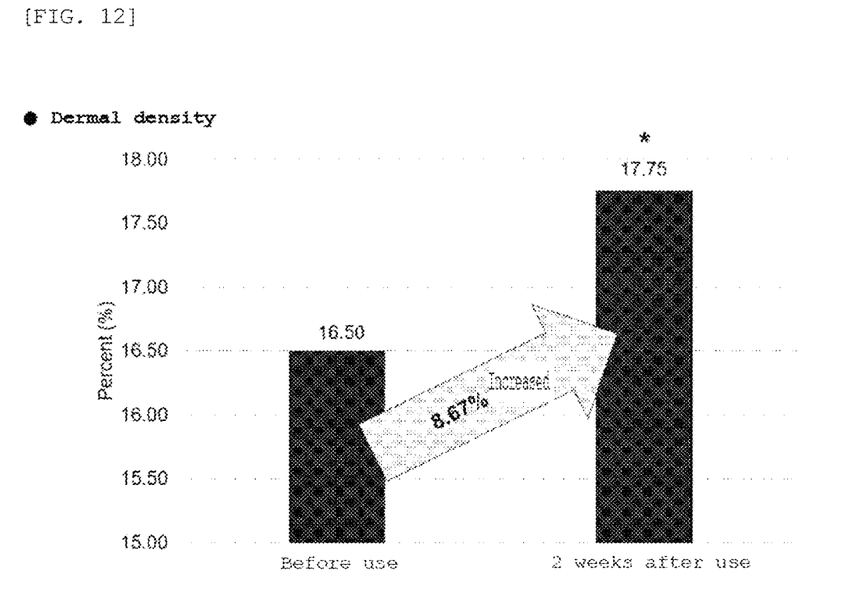
FIG. 12 is a graph showing the results of clinical tests on dermal density using the microneedle manufactured according to the embodiment of the present invention.
Figure 13:
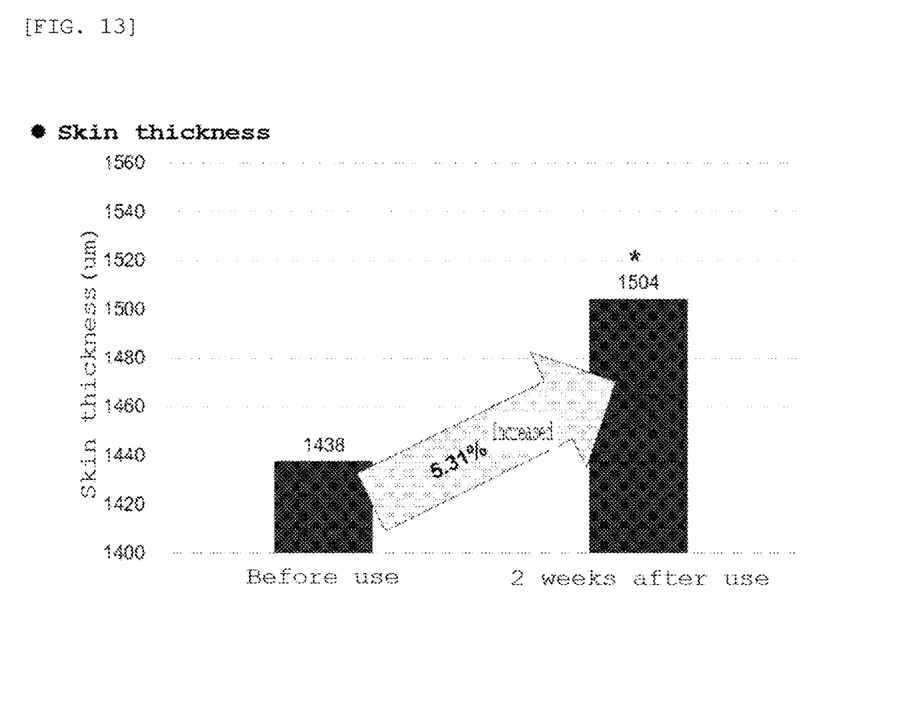
FIG. 13 is a graph showing the results of clinical tests on skin thickness using the microneedle manufactured according to the embodiment of the present invention.
Figure 14:
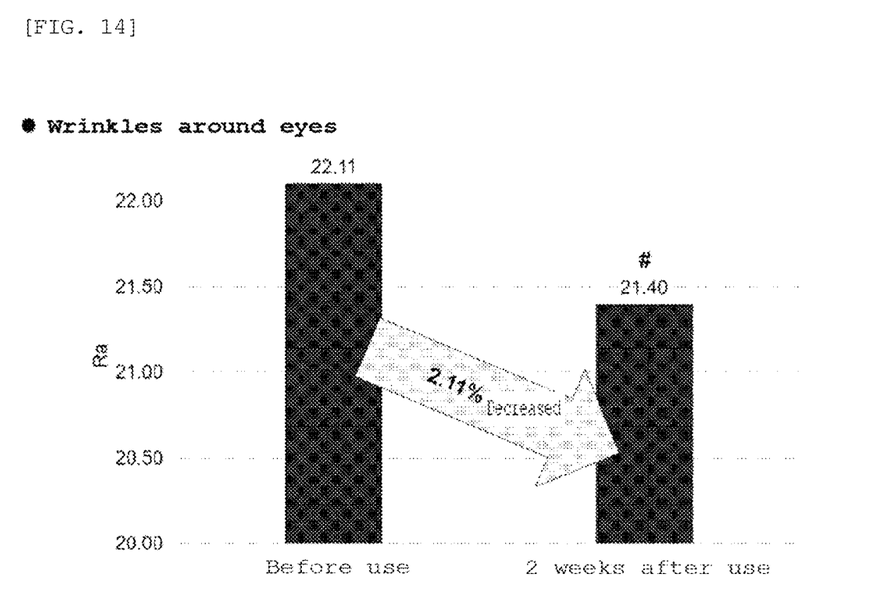
FIG. 14 is a graph showing the results of clinical tests on wrinkles around the eyes using the microneedle manufactured according to the embodiment of the present invention.

Clinical evaluation of the microneedle patch manufactured in Example 10 was performed. After the microneedle patch was applied to twenty female test subjects aged full 29 to 55 years who had wrinkles around the eyes and who met the selection criteria and did not accord with the selection exclusion criteria, it was checked whether the dermal density, skin thickness, and wrinkles around the eyes were changed before use and 2 weeks after use, and the average values of the results are shown in FIGS. 12 to 14.

Selection Criteria

1. A woman having wrinkles around eyes

2. A person who has listened to a complete explanation of information to be provided to the test subject by the person in charge of the test or by a person authorized by the person in charge of the test and has then voluntarily prepared and signed a consent form 3. A healthy person who does not have an acute or chronic physical disease, including a skin disease 4. A person who can be monitored during the test period Selection Exclusion Criteria 1. A person having a psychiatric disorder 2. A person having an infectious skin disease 3. A person who has undergone immunosuppressant therapy within 3 months before the start of the test 4. A person who has undergone systemic steroid therapy or phototherapy within 1 month before the start of the test 5. A person deemed difficult to measure due to a lesion in a test region The dermal density, skin thickness, and wrinkles around the eyes were measured using the methods shown in the following Tables 6 and 7.

TABLE 6

Measurement method of dermal density and skin thickness

| | |
|---|---|
| Test method | Skin scanner measurement |
| Test region | Skin surrounding eye |
| Measurement section | Before use and two weeks after use |
| DATA | Provision of numerical values |
| Note | Lefts side of face: microneedle patch + serum |
| | Right side of face: microneedle patch |

TABLE 7

Measurement method of wrinkles around eyes

| | |
|---|---|
| Test method | Ra analysis after primos premium photographing |
| Test region | Skin surrounding eye |
| Measurement section | Before use and two weeks after use |
| DATA | Provision of numerical values/images |
| Note | Lefts side of face: microneedle patch + serum |
| | Right side of face: microneedle patch |

Figure 15:
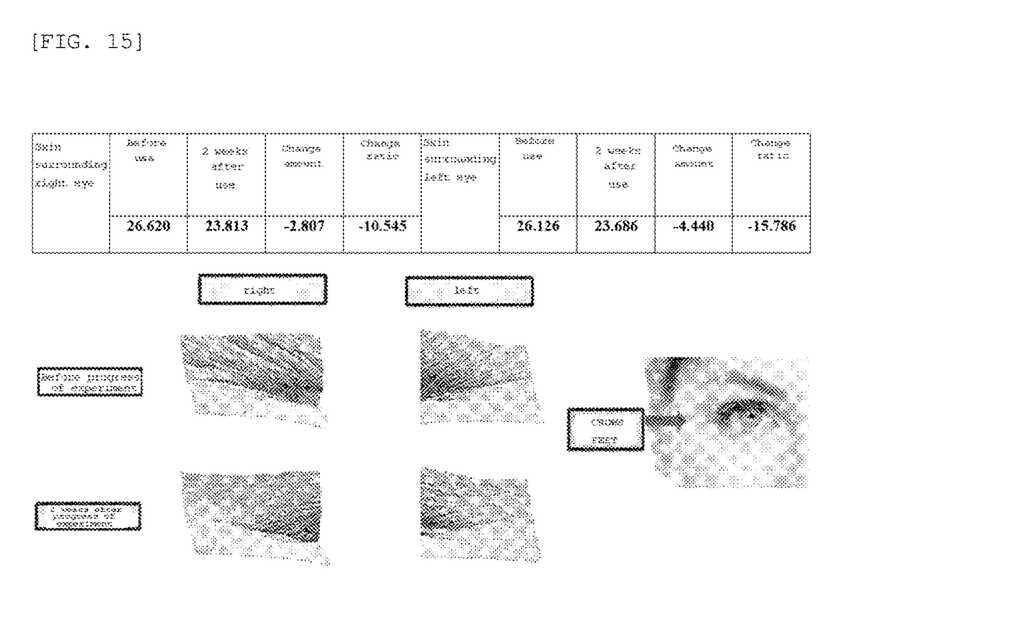
FIG. 15 is a photograph showing the results of clinical tests on wrinkles around the eyes using the microneedle manufactured according to the embodiment of the present invention.

※ Measurement condition: Measurement under constant temperature and humidity conditions As a result, as shown in FIGS. 12 to 14, the dermal density was increased by 8.67%, the skin thickness was increased by 5.31%, and the wrinkles around the eyes were decreased by 2.11% 2 weeks after the use thereof, compared to before the use of the microneedle patch. Further, it could be confirmed from the photograph of FIG. 15 that the wrinkles around the eyes were significantly reduced.

Experimental Example 5: Evaluation of Drug Delivery of Microneedle Sheet 5-1: Evaluation of Polymer Skin Infiltration Ability Lipstick was applied to the skin in order to evaluate the polymer skin delivery ability of the microneedle patch manufactured in Example 10, and the microneedle patch was attached thereto. After 30 minutes, the patch was removed, followed by washing. For reference, materials having a molecular weight of 500 da or more are not easily absorbed into the skin.

Figure 16:
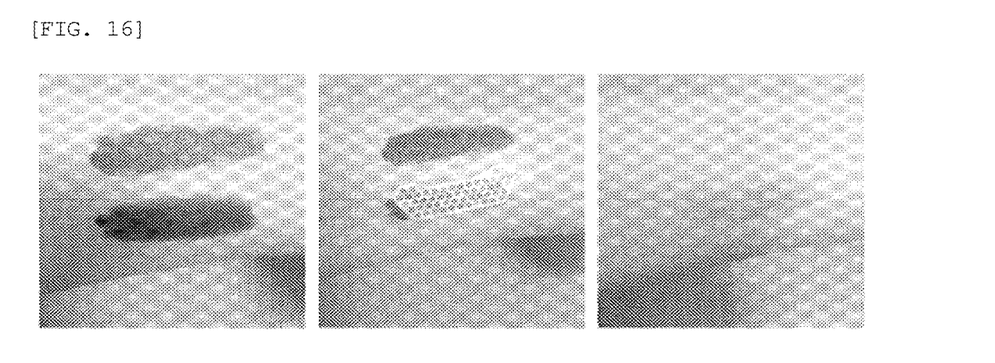
FIG. 16 is a photograph showing the evaluation of the polymer infiltration ability of a microneedle patch manufactured according to the embodiment of the present invention.

Accordingly, as shown in FIG. 16, when the microneedle patch was not attached, the lipstick was washed away because the lipstick was not absorbed. However, when the microneedle patch was attached, it could be confirmed that the lipstick was absorbed into the skin.

5-2: Evaluation of Drug Delivery Using Pig Skin

In order to evaluate the drug skin delivery ability of the microneedle patch manufactured in Example 10, a methylene blue dye was carried in place of the drug in the microneedle patch, followed by attachment to the pig skin. After the attachment, continuous pressure was applied thereto for 5 minutes to thus accelerate dye infiltration. After 30 minutes, the microneedle patch was removed, the cross section of the pig skin was cut, and the drug delivery ability was evaluated using an optical microscope.

Figure 17:
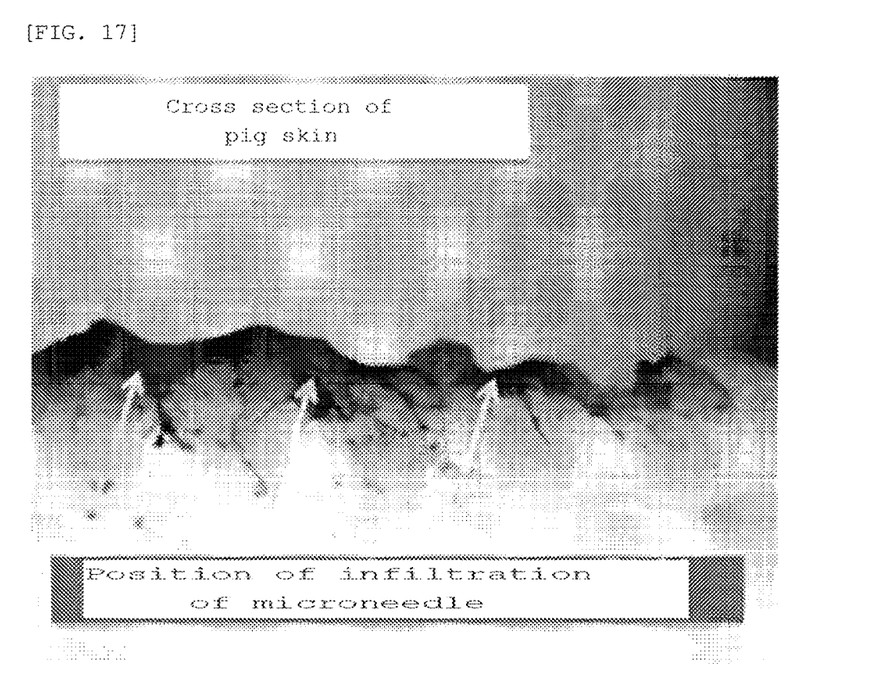
FIG. 17 is a photograph showing the evaluation of the drug infiltration ability of the microneedle patch manufactured according to the embodiment of the present invention.

From FIG. 17, it could be confirmed that the dye was deposited thickly at the place where the microneedle infiltrated.

While specific portions of the present invention have been described in detail, it will be understood by those skilled in the art that this specific technology is only a preferred embodiment, and that the scope of the present invention is not limited thereby. Therefore, the actual scope of the present invention will be defined by the appended claims and their equivalents.

INDUSTRIAL APPLICABILITY

The microneedle or the microneedle patch of the present invention may be utilized in prevention of diseases using vaccine delivery and in drug delivery for skin care, in addition to drug delivery for therapy.

The invention claimed is:

1. A method comprising:
   inserting to subcutaneous or epithelial tissue a microneedle; and
   increasing dermal density and skin thickness, wherein
   the microneedle comprises a biodegradable metal which is represented by Chemical Formula 1 and which is absorbed and degraded after the subcutaneous or epithelial insertion to thus release magnesium or zinc metal ions and degradation products comprising $H_2$ gas into a body:

$$Mg_a Zn_b X_c \qquad \text{[Chemical Formula 1]}$$

in Chemical Formula 1, where a is 96.85 to 96.9, b is 3, c is 0.1 to 0.15, and X is Ca, where a, b, and c represent wt % of respective ingredients, a+b+c=100 wt %.

2. The method of claim 1, wherein in the biodegradable metal, two or more metal phases generate a galvanic circuit to thus accelerate a degradation rate.

3. The method of claim 2, wherein the microneedle includes an $Mg_2Ca$ phase.

4. The method of claim 2, wherein the microneedle includes an MgZn phase.

5. The method of claim 1, wherein in the microneedle, a surface of a metal is coated with another type of second metal in order to form a galvanic circuit.

6. The method of claim 5, wherein the second metal is one or more metals selected from the group consisting of sodium, magnesium, potassium, iron, nickel, zinc, gallium, selenium, strontium, zirconium, molybdenum, niobium, tantalum, titanium, silicon, silver, gold, manganese, and calcium.

7. The method of claim 1, wherein the microneedle is coated with a drug or the drug is carried in the microneedle.

8. The method of claim 1, wherein the microneedle is a thin-plate type.

9. The method of claim 1, wherein a is 96.9 and c is 0.1.

10. The method of claim 1, wherein a is 96.85 and c is 0.15.

* * * * *